United States Patent [19]

Taylor et al.

[11] Patent Number: 4,969,379
[45] Date of Patent: Nov. 13, 1990

[54] DISPOSABLE NEEDLE AND SYRINGE DESTRUCTOR UNIT

[76] Inventors: Charles N. Taylor, 140 French St., Bristol, Conn. 06010; Martin H. Taylor, 28 Canal St., Plainville, Conn. 06062; Patricia A. Phillips, 8103 E. Lewis Ave., Scottsdale, Ariz. 85257; Norman R. Miner, 506 Washington Rd., Terryville, Conn. 06786

[21] Appl. No.: 516,680
[22] Filed: Apr. 30, 1990
[51] Int. Cl.$^5$ .................. B23D 15/00; B26D 5/10
[52] U.S. Cl. .................................. 83/167; 83/580; 83/944
[58] Field of Search ................ 83/944, 167, 580; 604/110; 206/364; 30/184, 131

[56] References Cited

U.S. PATENT DOCUMENTS

| | | | |
|---|---|---|---|
| 3,785,233 | 1/1974 | Robinson | 83/944 X |
| 4,255,996 | 3/1981 | Choksi et al. | 83/944 X |
| 4,275,628 | 6/1981 | Greenhouse | 83/944 X |
| 4,404,881 | 9/1983 | Hanifl | 83/944 X |
| 4,531,437 | 7/1985 | Szablak et al. | 83/165 |
| 4,565,311 | 1/1986 | Pugliese et al. | 83/944 X |
| 4,867,309 | 9/1989 | Germain | 83/167 X |

Primary Examiner—Paul A. Bell
Assistant Examiner—Kenneth E. Peterson

[57] ABSTRACT

An hygienically disposable needle and syringe destructor unit is designed for receiving and destroying used needles and syringes and retaining them within a hermetically sealed enclosure. The needle and syringe are broken in three parts to ensure non-use and are trapped within a fluid impervious container. A viewing window allows the operator to ascertain when the container is full and a sealable cover hermetically seals the needle and syringe access aperture so that the unit can be disposed of without fear of damage to the environment.

16 Claims, 4 Drawing Sheets

DISPOSABLE NEEDLE AND SYRINGE DESTRUCTOR UNIT

BACKGROUND OF THE INVENTION

With the advent of contagious diseases being transmitted with intentional and often times unintentional contact with a contaminated needle or syringe, it is important that such needles and syringes be destroyed and rendered non-usable immediately after use. U.S. Pat. No. 4,531,437 describes an efficient needle and syringe destructor whereby the needles and syringe devices are broken in several pieces to render the devices completely unusable. When the container of such devices becomes full, it is removed from the destructor for independent disposal.

It has been recently observed that such devices are appearing in landfills and waterways by careless disposal practices. Given the large use of such devices by hospitals, infirmaries, doctors' offices and rescue vehicles, it is important that the devices not only be rendered unusable but also be prevented from interfering with the environment by such landfill and waterway contamination.

Accordingly, one purpose of the instant invention is to provide a disposable needle and syringe destructor whereby the container itself is hermetically sealed and presents little or no danger to the environment.

SUMMARY OF THE INVENTION

A needle and syringe destructor is fabricated from a sealed container that includes a spring-biased piston accessible from the exterior of the container for contacting the needles and syringes and breaking them into several pieces. The piston interfaces with the container by means of a flexible sealant to thereby prevent transfer of fluids in or out of the container. The needle and syringe access aperture is provided with a cover that also includes a sealant. Attachment of the cover to the aperture causes the container to be hermetically sealed from the environment.

DESCRIPTION OF THE PREFERRED EMBODIMENT

Figure 1:
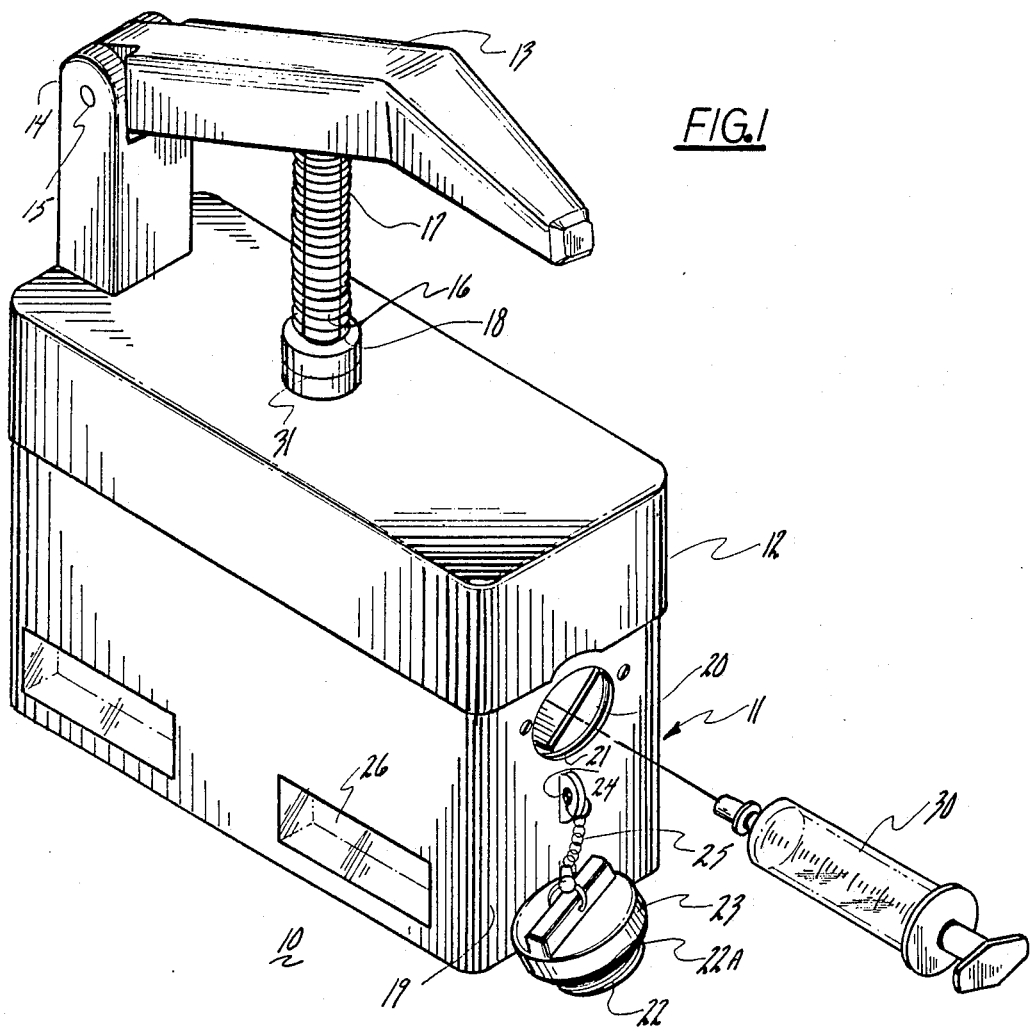
FIG. 1 is a top perspective view of the disposable needle and syringe destructor in accordance with the invention.

The destructor unit 10 shown in FIG. 1 consists of a container 11 of metal or thermoset plastic material that is closed by means of a cover 12 ultrasonically welded to form a weather-tight fit between the cover and the container. An operating handle 13 is supported on the cover by means of a handle support 14 and by means of a pivot pin 15. The handle is arranged over a piston 16 that enters the container through an opening 18 formed within a split collar 31 projecting from the cover. A hypodermic syringe 30 is placed within the container by insertion within an aperture 20 formed within the side 19 and is automatically positioned under the piston 16 for destruction in a manner to be described below. To seal the aperture when the container becomes full of crushed needles and syringes, a closure 23 fitted with an O-ring 22A is attached to the aperture by means of threads 22 on the closure and threaded opening 20 formed in the aperture.

To hold the closure to the container, a chain 25 attached to the closure at one end is attached to the container by means of a screw 24 at an opposite end. A pair of viewing windows 26 are formed within the unit to ascertain when the container is full of such crushed needles and syringes before the closure is threadingly attached to the aperture and the destructor unit is discarded.

Figure 2:
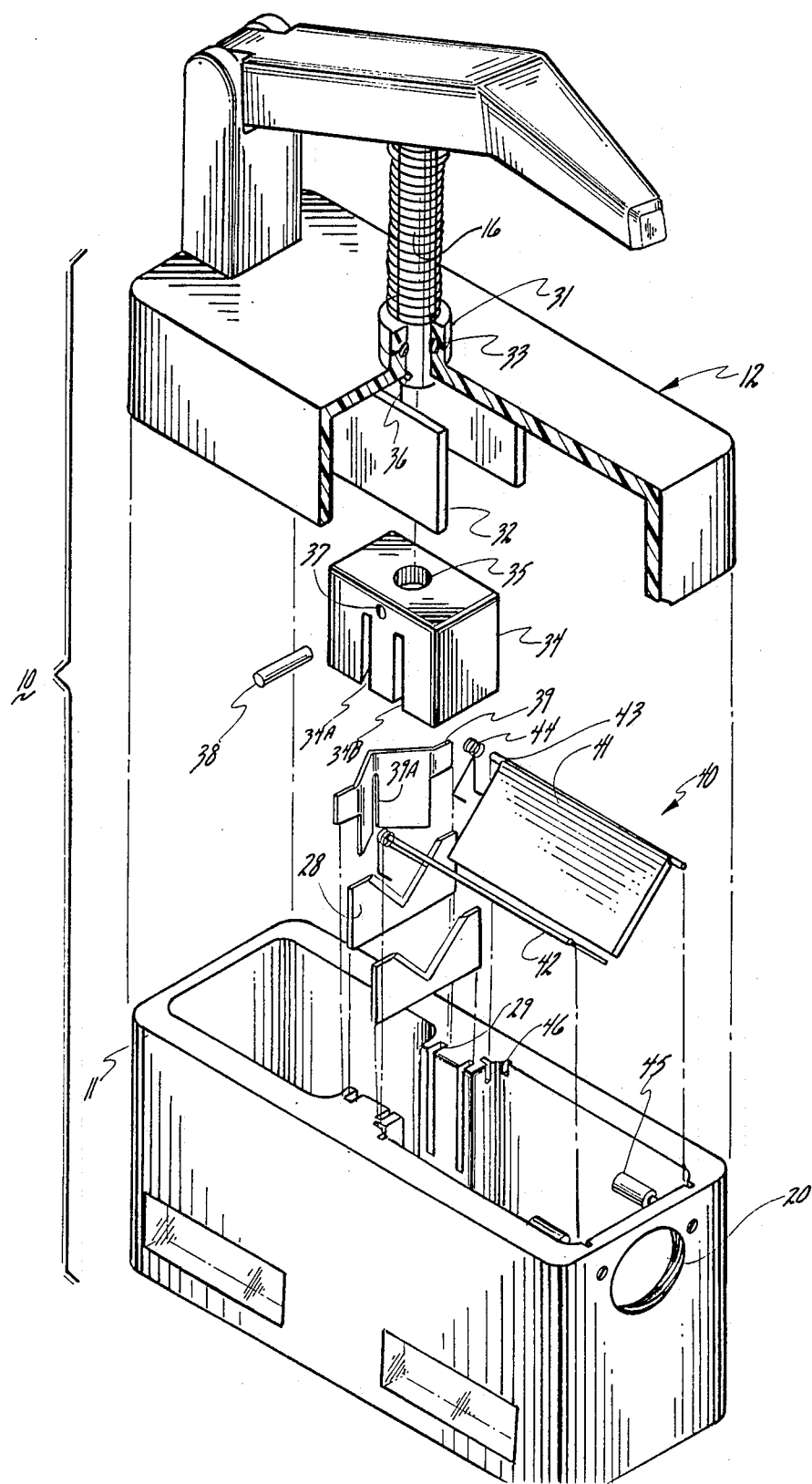
FIG. 2 is a top perspective view of the destructor of FIG. 1 in isometric projection.

The destructor unit 10 is assembled in the manner best seen by referring now to FIG. 2 wherein the cover is shown to include an O-ring 33 inserted within the split collar 31 to ensure that the piston moves in and out of the cover without permitting the transfer of fluids in or out of the unit when the cover is ultrasonically welded to the unit 10. A pair of parallel punch guides 32 are fastened to the underside top surface of the cover and a punch 34 is attached to the bottom of the piston by inserting the end of the piston within the opening 35 in the punch and aligning the thru-hole 36 formed in the end of the piston with the thru-holes 37 formed in the top of the punch. A pin 38 is pressed within both sets of thru-holes to fixedly attach the punch to the piston. A pair of V-shaped cutting dyes 28 are positioned within the container within corresponding slots 29 formed on the interior of sidewalls of the container and are positioned under corresponding elongated slots 34A, 34B formed in the bottom of the punch. A V-shaped stop member 39 is positioned within the container opposedly adjacent the aperture 20 to accurately position the needles and syringes over the V-shaped cutting dyes 28. A V-shaped trough 40, formed by means of a pair of side members 41, 42 is positioned within the container by arranging the posts 43 on opposite ends of the side members within corresponding slots 45, 46 integrally-formed within the container and within interposing shaped-springs 44 which bias the side members into the V-shaped closed configuration depicted in FIG. 2. The trough is arranged such that when the punch 34 crushes the needle and syringe against the V-shaped cutting dyes, the broken needle and syringe parts fall through the V-shaped trough in a "trap door" arrangement whereby the side members 41, 42 return to a closed position by means of the spring bias to receive and position the next needle and syringe.

Figure 3:
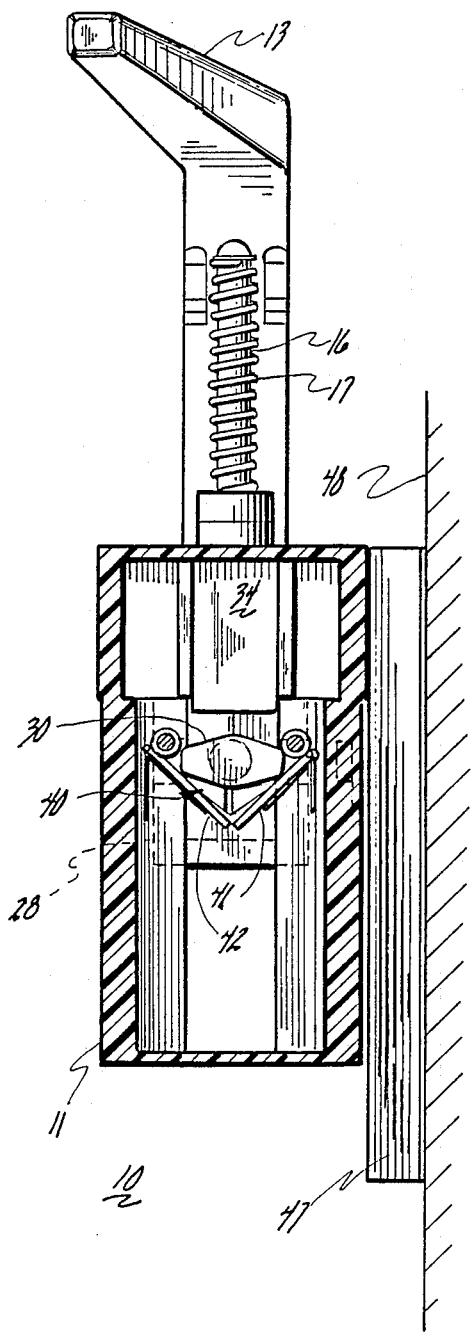
FIG. 3 is an end view of the destructor of FIG. 1 with the plunger in an inoperative position.
Figure 4:
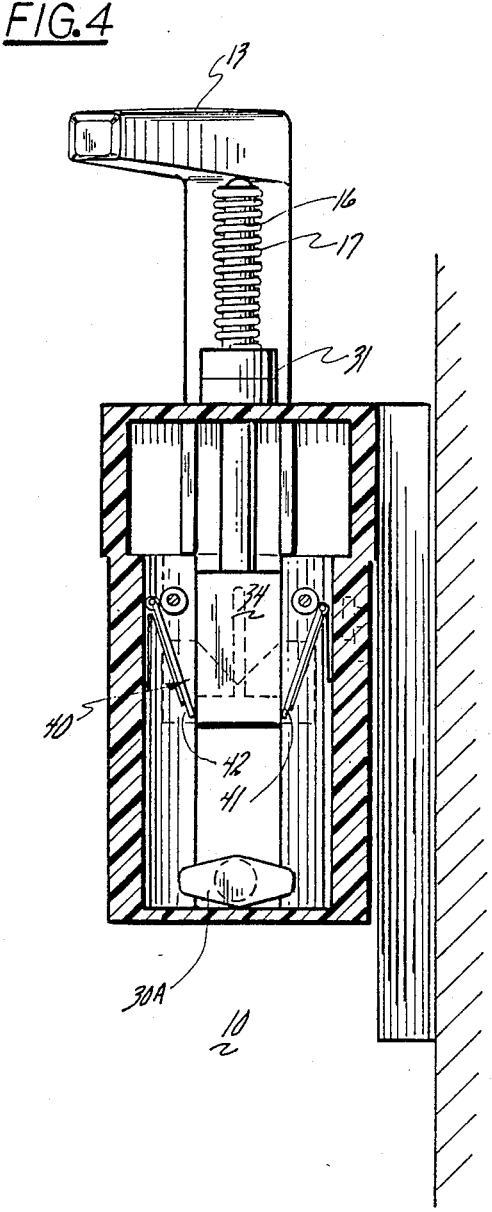
FIG. 4 is an end view of the destructor of FIG. 1 with the piston in an operative position.
Figure 6:
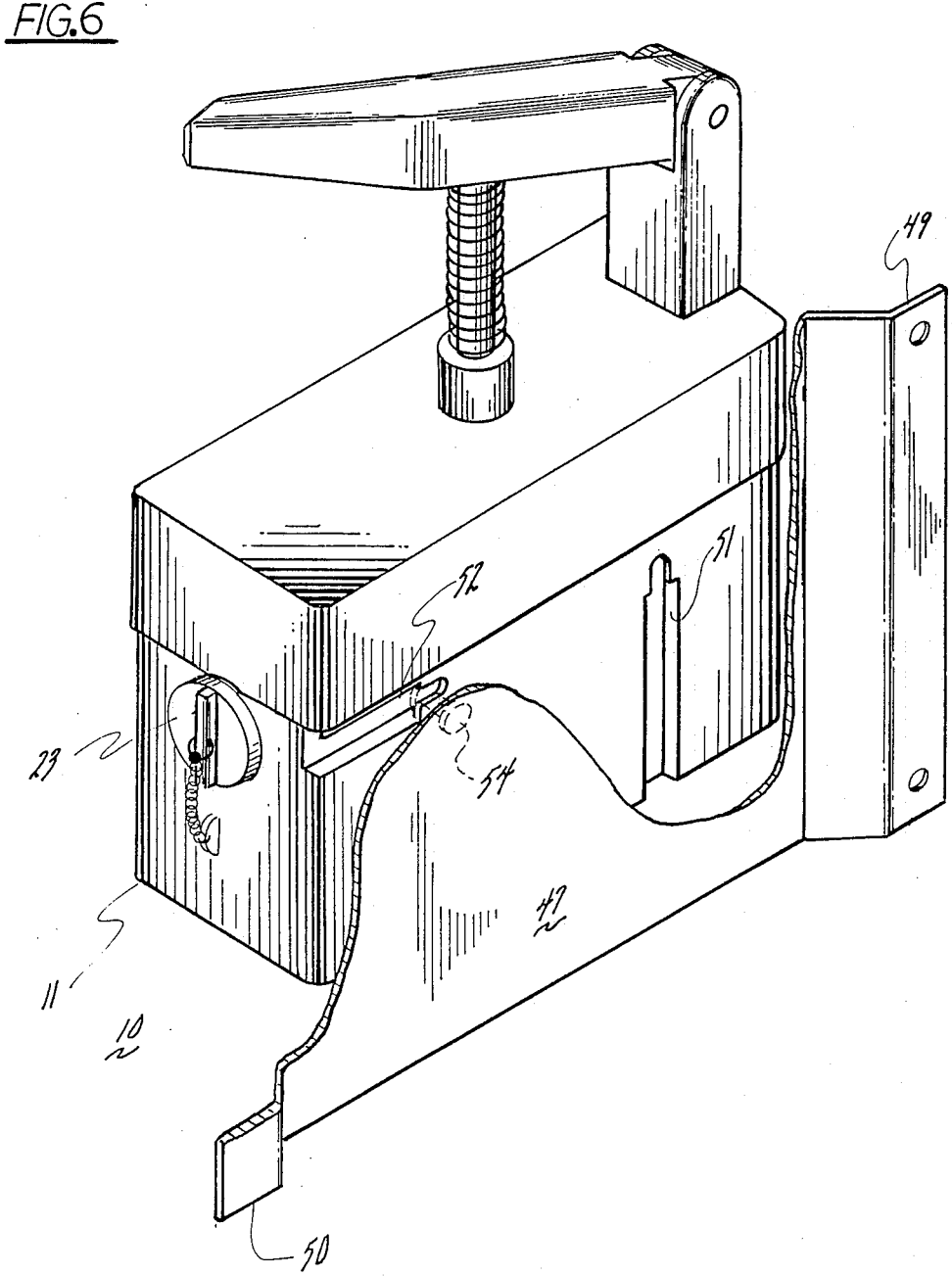
FIG. 6 is a side view of the destructor of FIG. 1 detailing the wall mounting facility.

The operation of the destructor unit 10 is best seen by referring now to FIGS. 3 and 4 wherein the unit is depicted attached to a sidewall 48 of a room in a medical facility by means of a metal mounting plate 47. A hypodermic syringe 30 is inserted within the container 11 and is positioned within the V-shaped trough over the sides 41, 42. This aligns the hypodermic syringe under the punch 34. Depressing the handle 13 now forces the piston 16 against the spring tension exerted by the spring 17 against the split collar 31 to thereby trap the hypodermic syringe between the cutting dyes 28 and the punch 34 and separates the sides 40, 41 allowing the broken hypodermic syringe to fall to the bottom of the container as depicted at 30A.

Figure 5:
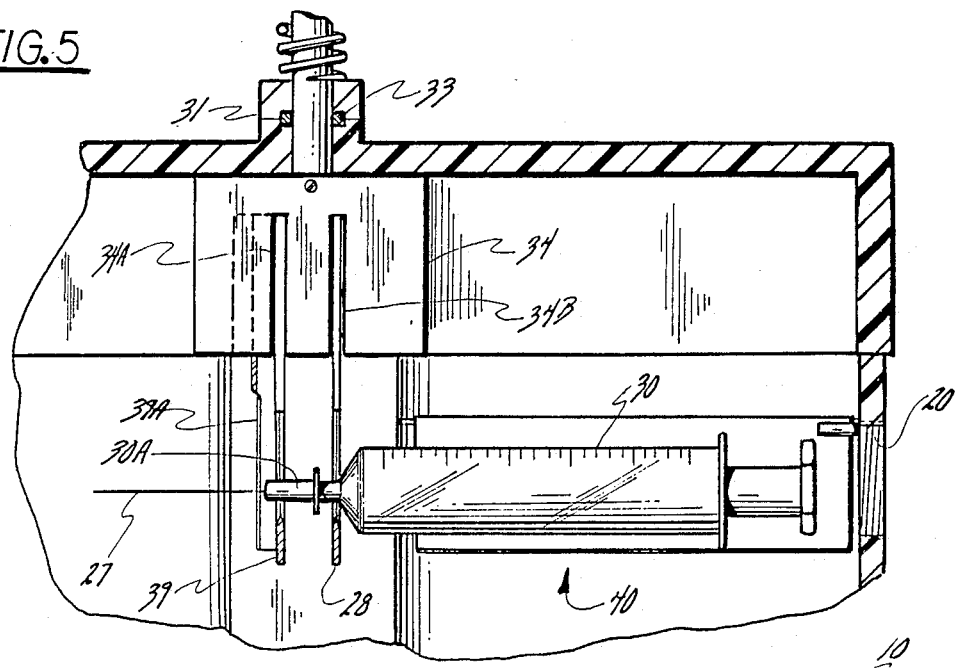
FIG. 5 is a partial side view of the destructor of FIGS. 3, 4.

The contact between the punch 34 and the hypodermic syringe 30 best seen by referring now to FIG. 5. The hypodermic syringe 30 is supported within the trough 40 immediately upon insertion of the hypodermic syringe within the aperture 20. The needle 27 at the end of the hypodermic syringe passes through the slot 39A within stop 39 causing the enlarged diameter 30A at the end of the needle to abut against the stop and to thereby position part of the needle and the hypodermic syringe between the elongated slots 34A, 34B on the punch 34 and the dyes 28. The hermetic seal between the unit and the piston is made by means of the O-ring 33 within the split collar 31.

The mounting arrangement between the destructor unit 10 and an adjacent wall is facilitated by the mounting plate 47 having a pair of offset ends 49, 50 containing a pair of thru-holes to facilitate use of mounting screws. A vertically arranged slot 51 and horizontally arranged slot 52 integrally-formed in the exterior surface of the container 11 receive corresponding projections 54 on the mounting plate and thereby provide removable attachment of the unit. When the unit is full of needles and syringes, the closure 23 is fastened to the container to provide a hermetic seal. The destructor unit is then removed from the mounting plate and is disposed of in accordance with both state and federal regulatory requirements without causing any damage to the environment.

Having thus described our invention, what we claim as new and desire to secure by Letters Patent is:

1. Apparatus for destroying needles and syringes comprising:
   container means including an opening at a top part thereof receiving a piston;
   handle means arranged on said top part and connected with said piston for driving said piston between first and second positions within said container;
   support means within said container adapted for receiving a needle and syringe, said support being arranged under said piston such that said needle or syringe becomes crushed when said piston forces said needle and syringe into contact with said support; and
   aperture means formed within a side of said container providing entry for said needle and syringe, said aperture including closure means whereby said aperture means becomes hermetically sealed for environmentally safe disposal of said container.

2. The apparatus of claim 1 including sealant means arranged around a part of said piston means intermediate said piston and said opening thereby allowing said piston to move between said first and second positions without allowing transfer of fluids in or out of said container.

3. The apparatus of claim 2 wherein said closure means comprises an aperture cover arranged for fastening to said container over said aperture to provide a hermetic seal to said aperture and thereby prevent transfer of said fluids in or out of said container.

4. The apparatus of claim 3 including sealant means arranged on said apertures cover intermediate said aperture cover and said aperture.

5. The apparatus of claim 1 wherein said handle is pivotally attached to said top part.

6. The apparatus of claim 5 including a spring associated with said piston to thereby bias said piston to said first position.

7. The apparatus of claim 5 wherein said top part comprises a container cover.

8. The apparatus of claim 7 wherein said container cover is attached to said container by welding.

9. The apparatus of claim 1 further including flexible means holding said aperture cover to said container.

10. The apparatus of claim 9 wherein said flexible means comprises a chain.

11. The apparatus of claim 7 wherein said support comprises a V-shaped configuration.

12. The apparatus of claim 11 wherein said piston includes a punch attached to one end.

13. The apparatus of claim 1 including a viewing window on one side of said container providing inside visual to said container.

14. The apparatus of claim 1 including guide means associated with said support to hold said needle and syringe until said punch crushes said needle and syringe against said support and thereafter allowing said crushed needle and syringe to drop into said container.

15. The apparatus of claim 14 wherein said guide means in spring-loaded to a closed position.

16. The apparatus of claim 15 wherein said support comprises a pair of sides arranged in a V-shaped configuration.

* * * * *